United States Patent [19]

Newman

[11] Patent Number: 4,944,947
[45] Date of Patent: Jul. 31, 1990

[54] THERAPEUTIC DENTAL APPLIANCE

[76] Inventor: Martin H. Newman, 77 Norwood St., Sharon, Mass. 02067

[21] Appl. No.: 186,449

[22] Filed: Apr. 26, 1988

[51] Int. Cl.[5] ............................................. A61K 7/18
[52] U.S. Cl. .................................... 424/435; 128/861; 521/119
[58] Field of Search ................ 523/115, 116; 424/435, 424/443; 434/5, 6; 128/859–862; 521/106, 119, 125; 433/5, 6; 264/16, DIG. 63; 106/35; 206/63.1

[56] References Cited

U.S. PATENT DOCUMENTS

| | | | |
|---|---|---|---|
| 2,589,504 | 3/1952 | Miller | 128/861 X |
| 2,750,941 | 6/1956 | Cathcart | 128/862 |
| 3,527,219 | 9/1970 | Greenberg | 128/861 X |
| 3,844,286 | 10/1974 | Cowen | 128/861 X |
| 3,955,281 | 5/1976 | Weitzman | 128/861 X |
| 3,969,499 | 7/1976 | Lee, Jr. et al. | 424/52 |
| 4,044,762 | 8/1977 | Jacobs | 433/6 X |
| 4,515,910 | 5/1985 | Rawls et al. | 523/115 |
| 4,572,920 | 2/1986 | Rawls et al. | 524/544 X |

Primary Examiner—Ellis P. Robinson
Assistant Examiner—Donald J. Loney
Attorney, Agent, or Firm—Robert F. O'Connell

[57] ABSTRACT

A new therapeutic polymeric foam dental appliance is disclosed for utilization in the treatment of teeth and/or gums, as well as a method of preparing said appliance by reaction of a polyurethane foam prepolymer with an aqueous treatment solution. A sterile, prepackaged therapeutic dental appliance in ready to use form by dental professionals is also disclosed.

14 Claims, 1 Drawing Sheet

THERAPEUTIC DENTAL APPLIANCE

BACKGROUND OF THE INVENTION

This invention relates to a new therapeutic polymeric foam dental appliance which can be utilized in the treatment of teeth, a method of preparing such an appliance, a method of providing therapeutic treatment for teeth utilizing such an appliance, and a sterile, prepackaged therapeutic appliance in a ready to use form for use by dental professionals.

During the first four decades of this century, the search for the etiologic factor responsible for endemic dental mottling in localized regions of the United States led to the discovery that fluoride is a potent cariostatic agent. Thereafter, it was determined that topically applied fluoride could reduce the rate of dental caries in many individuals. Today, a wide variety of fluoride-containing products are available for professional use. In addition to the many fluoride containing dentifrices and mouthwashes, there are a variety of dental trays which fit into the mouth and are used to apply a fluoride gel to the teeth.

A current problem with fluoride products which utilize fluoride gels which are applied to containers whose geometry resembles the general shape of the teeth is that an excess of fluoride is used which ultimately can pass into the gastro-intestinal tract, possibly resulting in acute fluoride toxicity. Victims of fluoride toxicity exhibit symptoms which include nausea, vomiting, and burning or cramp-like abdominal pains. Furthermore, there may be excessive salivation and tearing, mucous discharges from the nose and mouth, generalized weakness, paralysis of the muscles of swallowing, carpo-pedal spasms or spasms of the extremities, or tetany. In severe cases the patient may have convulsions, a weak pulse, lowered blood pressure, or depressed respiration.

Topical fluoride gels which are applied in trays that are generally shaped to the maxillary and mandibular arch are, in most cases, acidified with phosphoric acid to a pH of about 3.5 and are called APF (acidulated phosphate fluoride) gels and contain fluoride at concentrations of 1.23% or 12,300 ppm. In other words, each mL of gel contains 12.3 mg of fluoride. Most commonly, fluoride gels are supplied to the dentist in 500 mL bottles which contain over 6000 mg of fluoride. The gel trays are supplied separately and are filled individually for each treatment. The common fluoride gel treatment is applied to the dental arch for a period of four minutes. The average quantity of APF gel introduced into the mouth is in the vicinity of 5 mL, but may be as much as 12 mL, thus providing a corresponding amount of fluoride between 62 and 148 mg. A lethal fluoride overdose would be 60 mg or 4.9 mL for a two year old with an average body weight of 12 kilograms.

It has been demonstrated that the fluoride concentration at the enamel-oral interface is of critical importance in the dynamics of demineralization and remineralizaton (Fejerskov et al., Acta. Odontol. Scand. 39:241, 1981). Clearly, there is a relationship between fluoride concentration in the oral fluids and the action of fluoride on enamel and its environment. Numerous investigations (Le Compte and Doyle, J. Am. Dent. Assoc. 10:357, 1985; More et al., AADR Progr. & Abst. 62:837, 1983; Le Compte and Doyle, J. Dent. Res. 61:1397, 1982; Le Compte and Whitford, J. Dent. Res. 60:776, 1981, and 61:469, 1982; Ekstrand et al., Caries Res. 15:213, 1981; Ekstrand and Kock, J. Dent. Res. 59:1067, 1980; Owen et al., IADR Progr & Abst. 58: No. 1256, 1979; Ekstrand et al, Clin. Pharmacol. Ther. 23:329, 1978) have documented substantial oral retention and ingestion of fluoride following professional application of APF gels topically in children and adults.

The purpose of professional fluoride treatments is to benefit the tooth enamel by a topical effect. In an ideal topical application procedure, the patient would swallow no fluoride. In studies by LeCompte (J. Dent. Res. 66:1066, 1987), the amount of fluoride recovered from the mouth and that retained in the mouth were determined after four minute treatments. A foam-lined tray was used for the treatment with 49.2 mg of fluoride being applied to the teeth. An average of 39.3 mg of fluoride was recovered with the trays and 9.9 mg of fluoride was retained in the mouth. After one minute the patient expectorated an additional 6.8 mg of fluoride leaving a dose of 3.1 mg. Englander et al. (J. Am. Dent. Assoc., 75: 638, 1967) showed that less toxicity exposure resulted when smaller amounts of gel could be used in trays which were custom fitted to the teeth. Such custom trays required only five to ten drops because of the intimate contact between the tray and teeth surfaces. It is recommended that no more than two grams of gel be used in a gel tray application. Newbrun (J. Dent. Res. 66:1084, 1987) has suggested that the amount of fluoride gel should not exceed 1.5 grams.

In addition to the above mentioned toxicity problems, it has also been suspected that with current fluoride gel treatments, the gelling agents utilized may inhibit the efficient transfer of fluoride ions to the tooth surface.

SUMMARY OF THE INVENTION

In order to minimize patient exposure to excess fluoride or other therapeutics during treatment of the teeth and/or gums, applicant has developed a therapeutic containing polymeric foam dental appliance which is adapted to maintain intimate contact between the teeth and the appliance, allowing the therapeutic agent in the appliance to migrate to the tooth or gum surface. The dental appliance of the present invention is prepared by reacting in a mold a water-activated hydrophilic polymeric foam prepolymer, such as polyurethane foam prepolymer, with an aqueous treatment solution containing a treatment effective amount of a tooth or gum therapeutic composition, such as a fluoridating composition, to produce a foam polymer which contains the therapeutic composition (e.g. the aqueous fluoride) in the polymer structure. Treatment of teeth with the appliance of this invention results in efficient fluoride or other therapeutic uptake with only negligible exposure to the patient. In addition, gelling agents are eliminated which may otherwise interfere with therapeutic uptake or cause patient displeasure.

DETAILED DESCRIPTION OF THE PREFERRED EMBODIMENTS

Figure 1:
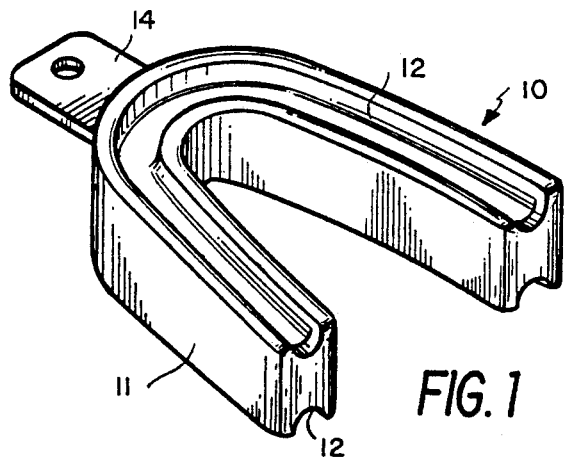
FIG. 1 is a perspective view of the dental appliance of the present invention.
Figures 2, 3, 4:
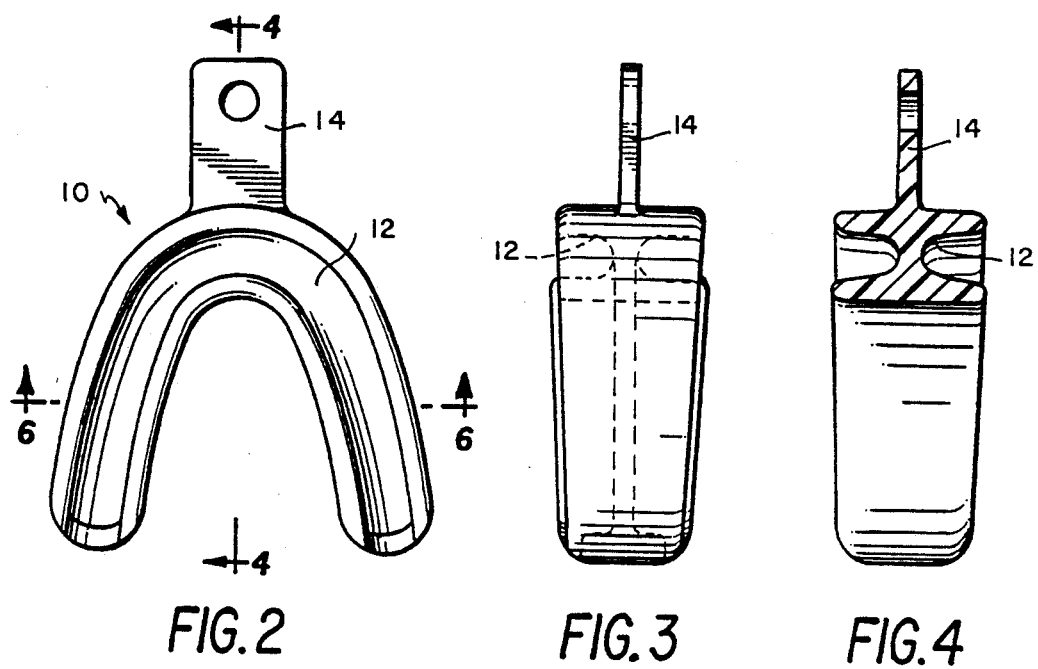
FIG. 2 is a top plan view of the appliance shown in FIG. 1.
FIG. 3. is a side elevational view of the appliance shown in FIG. 1.
FIG. 4. illustrates a cross-section of the appliance taken along line 4—4 of FIG. 2.
Figure 5:
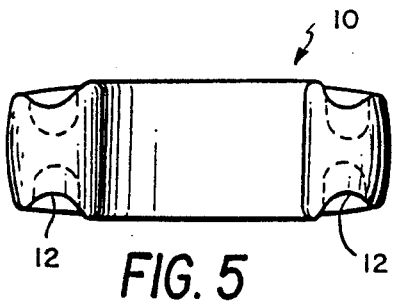
FIG. 5. is a front elevational view of the appliance shown in FIG. 1.
Figure 6:
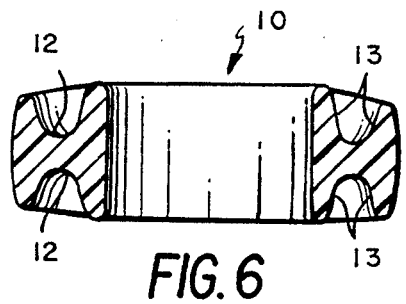
FIG. 6. illustrates a cross-section of the appliance taken along line 6—6 of FIG. 2.

Applicant has fabricated a therapeutic containing polymeric foam dental appliance with the configuration illustrated in FIGS. 1-6 of the drawings. This appliance is designed to intimately contact the surfaces of the teeth and/or gums and contains an effective amount of therapeutic agent, typically fluoride, in aqueous solution so that the teeth receive a uniform treatment. However, the water content is sufficiently low so that excess therapeutic agent does not flow into the patient's mouth where it can be subsequently swallowed.

With reference to the drawings, the dental appliance 10 comprises a polymeric foam block 11 which is generally horseshoe shaped to exactly conform to the teeth of the intended patient. This foam block contains recesses 12 extending along the length of the foam block on both sides thereof into which the patient's teeth are placed and in which the interior sides 13 of the recesses are spaced so as to maintain a close, if not snug, contact against the teeth (and optionally the gums) of the patient being treated. That is, the recesses are wide enough and deep enough so that the teeth/and or gums are substantially contacted by the foam block on at least two surfaces. Preferably, the depth and width of the recesses are varied in accordance with an exact anatomical model to achieve substantial compliance with the teeth. The appliance additionally contains a holding tab 14 extending outwardly from the midpoint thereof to facilitate handling of the appliance by the dental professional or patient.

The dental appliance of the present invention is fabricated of a flexible, hydrophylic polymeric foam material and is treated with a treatment effective amount of an aqueous therapeutic composition so that the appliance retains a sufficient amount of therapeutic agent for the treatment of teeth. A preferred polymeric foam material for use in fabricating the dental appliance is a polyurethane foam, most preferably a hydrophilic, open cell, cross-linked polyurethane foam. Preferred polyurethane foams are those that are derived from water-activated, hydrophilic polyurethane foam prepolymers, particularly isocyanate capped polyoxyethylene polyols with a hydroxyl number greater than 3, and particularly include those sold under the trademark HYPOL by W. R. Grace & Co., Organic Chemicals Div., Lexington, Mass. A particularly preferred prepolymer is HYPOL FHP 2002 because it produces a foamed polymer essentially free of extractable amines and isocyanates. The preferred polyurethane foam prepolymers generally comprise a polyoxyethylene polyol with a weight average molecular weight of about 200 to about 1500, preferably between about 600 and 1000, and a hydroxyl functionality of 3 or greater, preferably between 3 and 8, which has been capped with a diisocyanate or polyisocyanate to provide a prepolymer with an isocyanate functionality greater than 2. Such polyurethane foam prepolymers may be formulated, and foams may be prepared therefrom, in accordance with U.S. 3,903,232, the disclosure of which is incorporated herein by reference.

It has been found advantageous to prepare the polyurethane foam polymer and add the aqueous theapeutic agent all n one step. This can be accomplished by including the therapeutic composition (e.g. a fluoridating composition) as a solution in the reactant water which is reacted with the prepolymer to prepare the foamed product. Thus, a water-activated, hydrophilic polymeric foam prepolymer is mixed with an aqueous treatment solution containing a treatment effective amount of a therapeutic composition, and this polymer mix is allowed to react (i.e. foam) in a mold to form a foam block of predetermined shape. The resulting article may be sterilized for use as a dental therapeutic agent and packaged in a sterile, sealed package.

Generally, when the dental appliance of the present invention is intended for use in providing fluoride treatments, it will contain about 1 to about 4 grams of aqueous fluoride solution per gram of polymeric foam, preferably about 2 to about 2.5 grams of aqueous fluoride solution (1-2% fluoride).

In fabricating the therapeutic containing foam product of the invention, the quantity of water reacted with the prepolymer can be varied as desired between about 0.5:1 to 2:1 by weight (water: prepolymer), but is preferably reacted at approximately a 1:1 ratio. The amount of therapeutic composition in the reactant water should be an effective amount for providing the desired treatment. For a fluoride containing appliance, the fluoride ion level in the reactant water should be less than 3%, generally between about 0.5% and about 2.0%, preferably between about 1.0% and about 1.5% and most preferably about 1.23%, which is the level recommended by the American Dental Association. The preferred fluoride ion source is sodium fluoride, although other fluoride sources may be utilized. A most preferred aqueous fluoride solution which can be advantageously reacted with water-activated polyurethane foam prepolymers is an acidulated phosphate fluoride solution sold under the trademark NUPRO by Johnson & Johnson Dental Products Co. of East Windsor, N.J., which contains 1.23% fluoride ion (from NaF and HF) in 0.1M phosphoric acid solution.

In the case of a fluoride containing appliance, the pH of the reactant water should be adjusted to between 3.0 and 4.0, preferably about 3.5, since it has been found that this is the most effective pH for fluoride treatment. It is preferred to adjust the pH with phosphoric acid solution, typically about 0.1M concentration.

A surfactant may also optionally be incorporated into the reactant aqueous solution to control the porosity and wall thickness of the foamed article. Preferred surfactants are of the non-ionic type and include polyoxypropylene-polyoxyethylene block copolymers. Suitable surfactants include PLURONIC L-62 from BASF Corporation, Chemical Division, Parsippany, NJ and TERGITOL TMN-3 from Union Carbide Corp., Danbury, Conn. The surfactant(s) is generally added to the reactant water in an amount to provide about 0.5% to about 2.5%, preferably about 1%, surfactant per total reactants.

The foam appliance is formed in a mold based upon modified anatomical models available from Columbia Dentoform Corporation of New York, N.Y. The form of the appliance is anatomically accurate, thereby accommodating the anatomical differences in mandibular and maxillary dentin. Furthermore, the foam is fabricated to anticipate occlusion and make simultaneous contact of both mandible and maxilla. In addition, the taper from crown to gingival margin is slightly smaller than the tooth anatomy. Each of the described anatomically formed features of the appliance is engineered to insure compliance between the foam and the tooth and or/gum surface. The purpose of the foregoing is to cause the therapeutic agent which has been isolated within the foam during formulation (and optionally fortified thereafter with additional treatment solution if desired) to transfer by osmotic gradient differential to the surface of the tooth enamel and dentin. The availability of fluoride ions has been proven to occur in clinical tests, and such clinical tests have also shown an improved fluoride uptake in comparison to current gel products.

The foam dental appliance of the present invention is particularly advantageous in that it contains a low volume of low viscosity aqueous treatment solution that will readily irrigate and treat the interproximal areas (i.e., areas between the teeth) which would not otherwise be reached by a typical gel formulation. In the case of the fluoridated appliance, there is improved fluoride uptake in teeth with substantially reduced fluoride exposure to the patient.

EXAMPLE

In a plastic beaker was added 95.917 g of distilled water and 2.520 g of sodium fluoride and the mixture was stirred until all the sodium fluoride dissolved into solution. To this solution was added with stirring 1.180 g of concentrated phosphoric acid (85%), then 0.206 g of concentrated hydrofluoric acid (47.5%), and the solution was mixed thoroughly. The pH was adjusted to 3.2 to 3.5 with additional phosphoric acid, if necessary, to yield a 0.1M phosphoric acid solution containing 1.24% of free fluoride ion.

To 42 grams of the fluoride solution was added 2.1 grams of Pluronic L-62 surfactant with stirring to insure adequate mixing of the surfactant into the fluoride solution. This aqueous liquid mixture was then added to 42 grams of HYPOL FHP 2002 polyurethane foam prepolymer, which had been been preheated to 110° F., and the reaction mixture was stirred vigorously until it became frothy and cream colored. This mixture was dispensed into molds which had been preheated to 100° F. by measuring 2.5 grams ±0.5 gram into each half of the mold, then the molds were closed and clamped. After a 5 minute time period the molds were opened and the product removed to yield an aqueous fluoride containing polyurethane foam dental appliance as shown in FIG. 1.

The therapeutic dental appliance of the present invention may advantageously be sterilized and packaged in a sterile, moisture impermeable package, preferably one appliance per package, so that the appliance is available in a ready to use form by the dental professional or patient without any need to add further components, such as the fluoride gel which must be added to current products. The unit-dose package assures proper dosage and ease of use.

Ideally, the product should be packaged immediately after manufacture to prevent any degradation such as the loss of HF ion and change in the pH. Any suitable packaging materials may be employed that are capable of retaining moisture and maintaining the pH of the product, as well as maintaining a sterile environment. One such packaging material that has been found to be suitable is aluminium foil which is greater than 2.5 mils thick and which is coated with polyethylene. The package is heat sealed with the product inside. Another suitable packaging material can be fabricated of BAREX 210 resin (Standard Oil Company).

A patient may be treated with the therapeutic dental appliance of the present invention by simply inserting the appliance into the patient's mouth where it will substantially contact the surfaces of the patient's teeth and/or gums and maintaining it there for a sufficient time, generally 1 to 4 minutes in the case of fluoridation, to provide an effective therapeutic treatment.

While the invention has been described with respect to its preferred embodiments, it is understood that the invention is not to be limited thereby, but includes a range of equivalent materials, components and designs which would be apparent to those skilled in the art. For example, the dental appliance of this invention may readily be used to apply a variety of teeth or gum treating therapeutic compositions in addition to fluoridating compositions, such as plaque or tartar control agents, cleansing agents, whitening agents, anti-bacterial agents, anti-fungal agents, medicaments to treat tooth or gum disease, etc. The scope of the invention to be protected is defined by the claims which follow.

What is claimed is:

1. A dental appliance useful for treating teeth or mouth tissue, said appliance being in the form of a sterilized block of foam material comprising a mixture of a water-activated, hydrophilic foam prepolymer with an aqueous treatment solution containing a treatment effective amount of a therapeutic composition, said block having a predetermined shape containing said aqueous treatment solution for use as a dental therapeutic device.

2. The dental appliance of claim 1 wherein said polymeric foam prepolymer is a polyurethane foam prepolymer.

3. The dental appliance of claim 2 wherein about 0.5 to 2.0 parts of aqueous treatment solution are reacted with about 1.0 part of polyurethane foam prepolymer.

4. The dental appliance of claim 3 wherein said therapeutic compositon is a fluoridating composition.

5. The dental appliance of claim 4 wherein said aqueous treatment solution has a pH between about 3.0 to about 4.0.

6. The dental appliance of claim 5 wherein said aqueous treatment solution contains less than 3% by weight fluoride.

7. The dental appliance of claim 6 wherein said polyurethane foam prepolymer is a diisocyanate or polyisocyanate capped polyoxyethylene polyol with an isocyanate functionality greater than 2.

8. The dental appliance of claim 7 wherein said polyurethane foam prepolymer is selected from those that produce foams having no extractable amines or isocyanates.

9. The dental appliance of claim 8 wherein said aqueous treatment solution is an acidulated phosphate fluoride solution comprising about 1.0 to 1.5% fluoride by weight in 0.1M phosphoric acid solution, adjusted to a pH between 3.0 and 4.0.

10. The dental appliance of claim 9 wherein said aqueous treatment solution additionally contains a non-ionic surfactant in an amount to provide up to 2.5% surfactant by weight of total reactants.

11. The dental appliance of claim 10 wherein said polyurethane foam prepolymer is an isocyanate capped polyoxyethylene polyol with a hydroxyl number greater than 3.

12. The dental appliance of claim 11 wherein said aqueous treatment solution comprises 1.23% fluoride, 1% non-ionic surfactant and has a pH of about 3.5.

13. The dental appliance of claim 12 wherein said surfactant is a polyoxypropylene-polyoxyethylene surfactant.

14. The dental appliance of claims 1, 2, 3, 4, 5, 6, 7, 8, 9, 10, 11, 12, or 13 and further including a sterile sealed package into which said block of foam material is placed.

* * * * *